овый

United States Patent [19]
Mine

[11] Patent Number: 5,971,927
[45] Date of Patent: Oct. 26, 1999

[54] ULTRASONIC DIAGNOSTIC APPARATUS FOR OBTAINING BLOOD DATA

[75] Inventor: Yoshitaka Mine, Tochigi-ken, Japan

[73] Assignee: Kabushiki Kaisha Toshiba, Kawasaki, Japan

[21] Appl. No.: 08/953,994

[22] Filed: Oct. 20, 1997

[30] Foreign Application Priority Data

Oct. 21, 1996 [JP] Japan ..................................... 8-278186

[51] Int. Cl.$^6$ ...................................................... A61B 8/06
[52] U.S. Cl. ............................................................ 600/455
[58] Field of Search .................................. 600/454, 455, 600/472, 453, 450, 447; 367/7; 73/626

[56] References Cited

U.S. PATENT DOCUMENTS

| | | | |
|---|---|---|---|
| 5,417,219 | 5/1995 | Takamizawa et al. ................... | 600/472 |
| 5,419,332 | 5/1995 | Sabbah et al. ............................ | 600/455 |
| 5,456,255 | 10/1995 | Abe et al. ................................. | 600/443 |
| 5,469,849 | 11/1995 | Sasaki et al. ............................. | 600/458 |
| 5,485,844 | 1/1996 | Uchibori .................................. | 600/455 |
| 5,551,434 | 9/1996 | Iinuma ..................................... | 600/455 |

*Primary Examiner*—Francis J. Jaworski
*Assistant Examiner*—Ali M. Imam

*Attorney, Agent, or Firm*—Oblon, Spivak, McClelland, Maier & Neustadt, P.C.

[57] ABSTRACT

An interested region including an interested blood vessel of a subject is scanned by a plurality of ultrasonic waves so as to receive a plurality of echo signals. A plurality of Doppler signals is detected from the echo signals in connection with a plurality of sample points in the interested region. An average frequency of the blood current of the interested blood vessel, variance, and power are calculated based on the Doppler signals. A sample point positioned on the interested blood vessel is picked up from the plurality of samples every time phase based on the average frequency or power. A time curve is formed based on at least one of the average frequency of the picked up sample point, the variance, and power. Thereby, it is possible to compensate for the state that a sample volume is detached from the interested blood vessel as in the conventional case. After plural Doppler images were in a Doppler memory by 'Freeze' operation, a ROI is set on the memorized images and a spectrum Doppler image for blood vessels in the ROI is formed. The ROIs are set on images while confirming moving blood vessels. A change of the velocity of the vessels is observed. Indexes such as an RI (Resistance Index) are calculated and help a diagnosis.

27 Claims, 10 Drawing Sheets

_5,971,927_

ULTRASONIC DIAGNOSTIC APPARATUS FOR OBTAINING BLOOD DATA

BACKGROUND OF THE INVENTION

1. Field of the Invention

The present invention relates to an ultrasonic diagnostic apparatus for obtaining blood data by use of Doppler effect.

2. Discussion of the Background

FIG. 1 shows the structure of a conventional ultrasonic diagnostic apparatus corresponding to a spectrum Doppler mode. In this figure, a pulse generator 121 generates a rate pulse at a period of a reciprocal number of a pulse repetition frequency (PRF). A pulser 103 generates a voltage pulse having a high frequency in synchronous with the rate pulse. A piezoelectric vibrator of a probe 101 is vibrated by the voltage pulse. Thereby, an ultrasonic pulse is transmitted to a subject. A central frequency (transmission frequency) of the ultrasonic pulse is expressed by c.

The ultrasonic pulse is reflected at a boundary of acoustic impedance of the subject, and the part of the reflected ultrasonic wave is returned to the probe 101. Though the ultrasound is weak, the ultrasound scatters even in blood corpuscles. Since the blood corpuscles are moved, the frequency of the ultrasound is shifted in accordance with the velocity of the corpuscles. The spectrum Doppler mode observes the shifted frequency fd. The frequency fd can be obtained by the following equation:

$$fd = (2 \cdot V \cdot fc \cdot \cos \theta)/C$$

wherein a blood velocity is V, an angle between an ultrasonic beam and a direction of a blood current is $\theta$, and a sound velocity of a living body (about 1530 m/sec) is C. The center frequency of the ultrasound is fc.

To obtain the shift frequency fd of the blood current, an echo signal is amplified by a preamplifier 105 and orthogonally detected through a mixer 107 and a low pass filter 109. Thereby, a Doppler signal corresponding to a shift frequency component can be obtained.

Then, the Doppler signal from the depth of a sample volume 101 is time-gated by a range gate 119. The gated Doppler signal is supplied to a fast Fourier transformer (FFT) 115 through a sample hold circuit 111, and a band pass filter 113. The FFT 115 Fourier transforms 128 Doppler signals, which can be obtained by repeating transmission and receiving the signals 128 times for the period of 1/PRF. Thereby, power for each frequency component, frequency spectrum, can be obtained. Such a frequency spectrum is arranged along a time axis as shown in FIG. 2, and displayed on a monitor 117 with brightness in accordance with power. Since such an image is often called a spectrum Doppler image, the name spectrum Doppler image is used hereinafter.

An observer can obtain various data from the spectrum Doppler image. There are indexes such as an RI (Resistance Index), a PI (Pulsatility Index) other than information directly obtained from the Doppler image. For example, RI can be obtained by dividing a difference between a maximum velocity (maximum frequency) and a minimum velocity (minimum frequency) in one cardiac cycle by the maximum velocity. PI can be obtained by dividing a difference between the maximum velocity and an average velocity (average frequency) in one cardiac cycle by the average velocity. Most of indexes can be calculated by substituting a characteristic value extracted from the spectrum Doppler image for a predetermined equation.

However, the operation for calculating the indexes has the following problems:

(1) Since an operator must extract the characteristic value from the spectrum every time phase, a long processing time is required.

(2) The spectrum is lifted up by a contrast enhance effect of contrast enhance agent as shown in FIG. 3. As a result, the maximum frequency is shifted, and the value of the index is changed.

(3) As shown in FIG. 4, there is a case in which a sample volume is detached from an interested blood vessel by influence of a motion such as a breath motion, a pulsation, etc. In this case, the index is regarded as an error.

BRIEF SUMMARY OF THE INVENTION

An object of the present invention is to provide an ultrasonic diagnostic apparatus for forming a time curve of a blood current by a new method.

According to the present invention, an average frequency of a plurality of sample points in an interested region is calculated. Then, a sample point positioned on the interested region is picked up from the plurality of the sample points based on the average frequency. As a result, it is possible to compensate for the state that a sample volume is detached from the interested blood vessel as in the conventional case.

Also, according to the present invention, there is used an auto-correlation method, thereby making it possible to form a time curve of a blood current obtained from an FFT Doppler waveform as in the conventional case.

Moreover, according to the present invention, a plurality of time curves of the blood current at a plurality of sample points in the interested region are formed and displayed simultaneously, thereby making it possible to obtain new and useful data.

Moreover, after plural Doppler images were in a Doppler memory by 'Freeze' operation, an ROI is set on the memorized images and a spectrum Doppler image for blood vessels in the ROI is formed.

The ROIs are set on images while confirming moving blood vessels. A change of the velocity of the vessels is observed. Indexes such as an RI (Resistance Index) are calculated and help a diagnosis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention, in which.

DETAILED DESCRIPTION OF THE INVENTION

An embodiment of the present invention will now be described with reference to the accompanying drawings.

Figure 1:
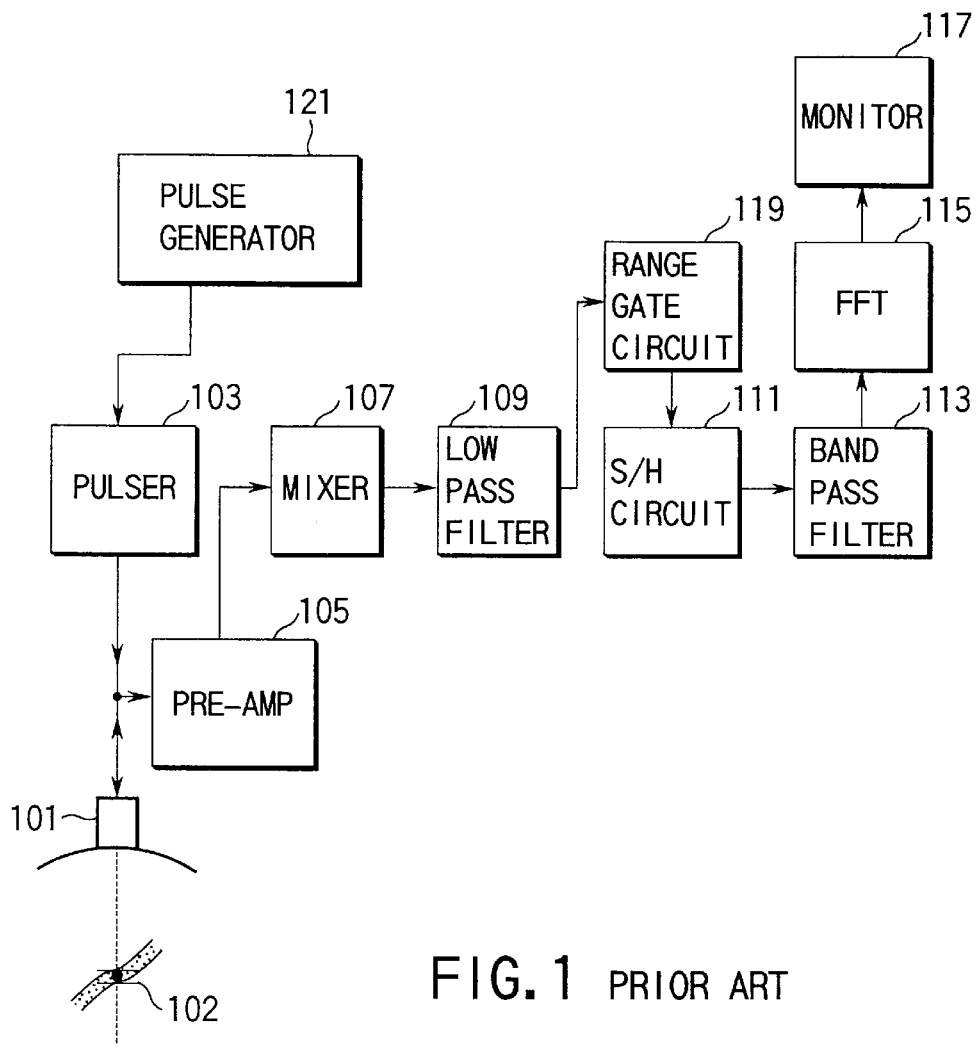
FIG. 1 is a block diagram of a conventional ultrasonic diagnostic apparatus for a spectrum Doppler.
Figure 2:
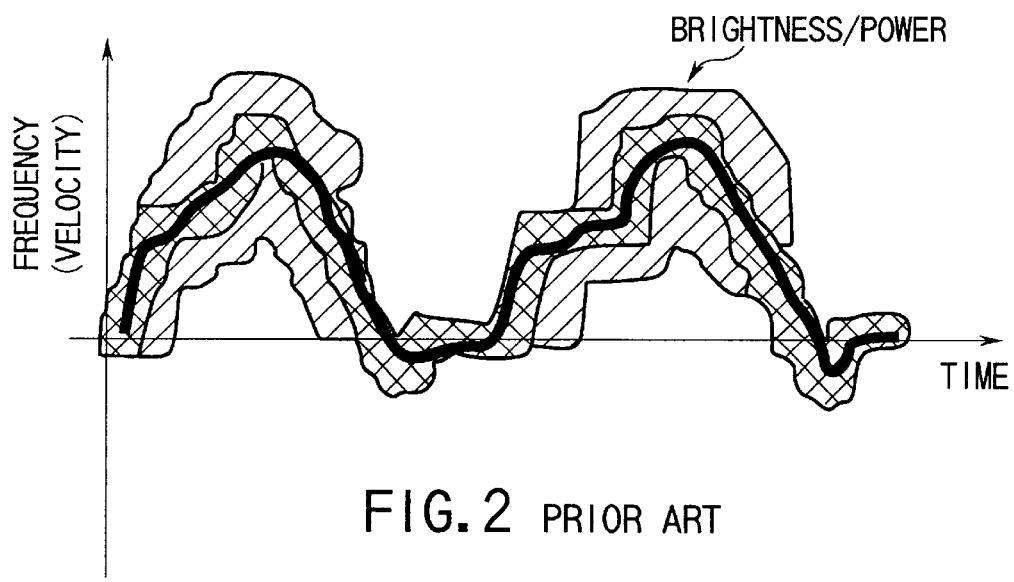
FIG. 2 is a view showing a conventional Doppler image.
Figure 3:
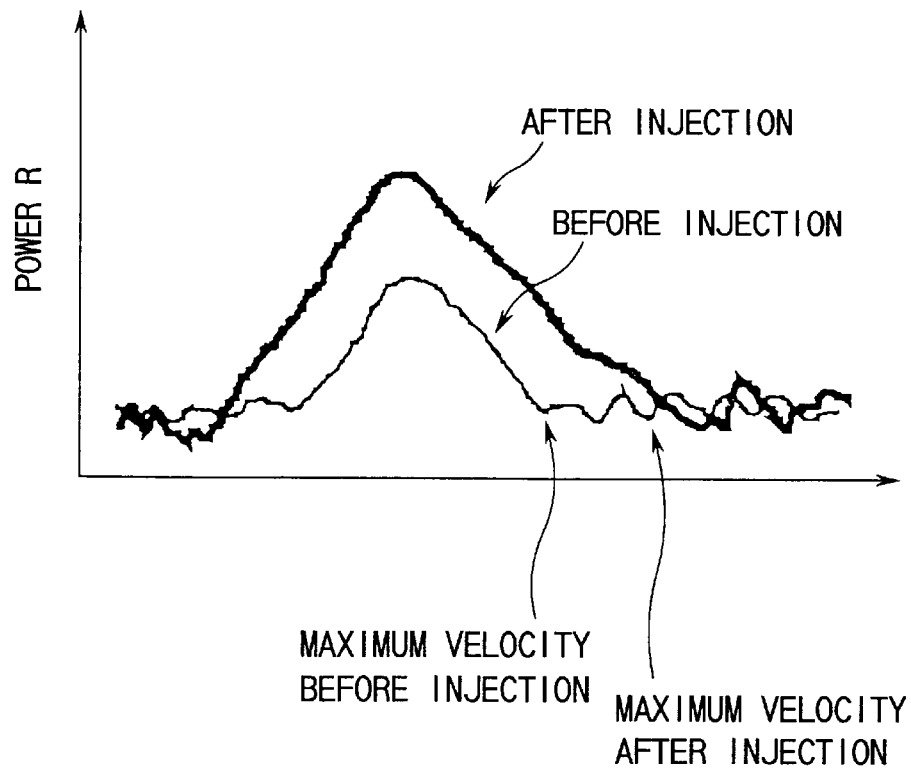
FIG. 3 is a view showing a state that a spectrum is lifted up by a contrast enhance effect.
Figure 4:
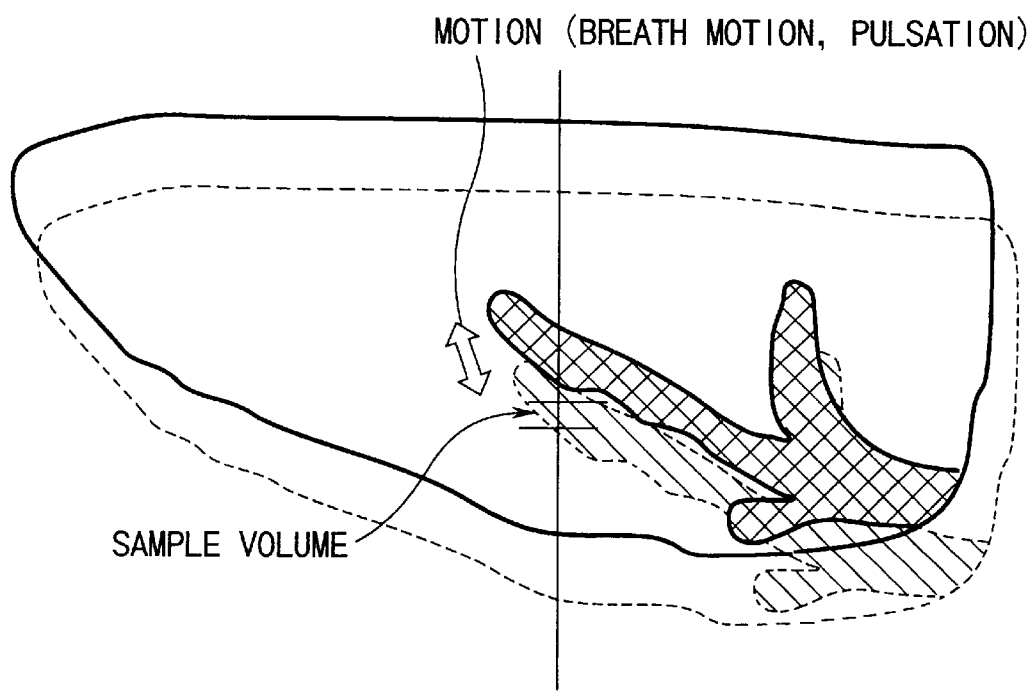
FIG. 4 is a view showing a state that a sample volume is detached from an interested blood vessel.
Figure 5:
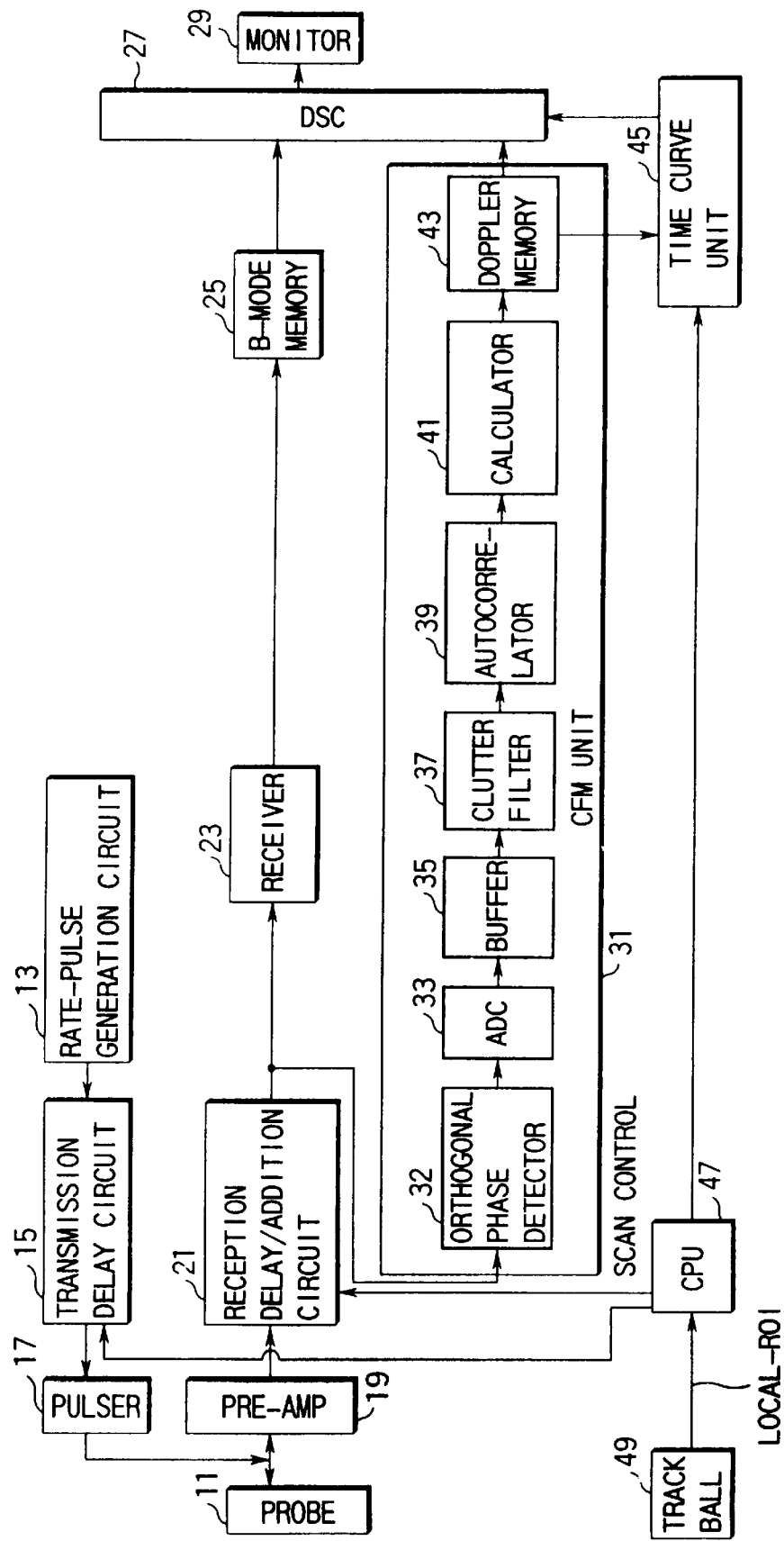
FIG. 5 is a block diagram of an ultrasonic diagnostic apparatus of the present invention.

FIG. 5 shows the structure of the ultrasonic diagnostic apparatus of the present invention. A probe 11 has a plurality of arrayed vibrators. A rate pulse generation circuit 13 generates a rate pulse in accordance with a pulse repetition frequency PRF of e.g. 6 KHz. A transmission delay circuit 15 delays the rate pulse. A pulser 17 generates a voltage pulse having a frequency $f_0$ in synchronous with the delayed rate pulse. The voltage pulse vibrates the vibrators. Thereby, an ultrasonic pulse whose central frequency is $f_0$ is transmitted to a subject.

The ultrasonic pulse is scattered at a boundary of acoustic impedance of the subject, and the part (echo) of the ultrasonic pulse is returned to the probe 11. Information of the impedance difference is contained in power of the echo. Velocity information of a moving object such as blood is contained in the Doppler frequency of the echo.

The vibrators of the probe 11 convert the echoes to electrical signals. A preamplifier 19 amplifies the electrical signals. A reception delay/addition circuit 21 delays the amplified electrical signals, and adds up these signals. The added signal is referred to as an echo signal. In the echo signal, the echo component from the direction in accordance with delay time is emphasized. The echo signal is sent to a receiver 23 and a color flow mapping unit (CFM unit) 31.

The receiver 23 logarithmically amplifies the echo signal, and detects an envelope. A detected signal is sent to a monitor 29 through a B mode memory 25 and a digital scan converter (DSC) 27 so as to be displayed as a B mode image (tissue tomographic image).

A CFM unit 31 comprises an orthogonal phase detector 32, an analog-digital converter (ADC) 33, a buffer 35, a clutter filter 37, an auto-correlator 39, and a calculator 41. The orthogonal phase detector 32 mixes a reference signal ($f_0$) and a reference signal ($f_0$) whose phase is shifted at 90° with the echo signal, separately. As a result, a Doppler shift frequency component $f_d$ and a high frequency component ($2 \times f_0 + f_d$) are extracted. Then, the orthogonal phase detector 32 removes the high frequency component from each of the signals, so that two kinds of Doppler signals, each having only a Doppler shift frequency component fd, are detected.

The analog-digital converter 33 samples the Doppler signals in accordance with a predetermined sampling frequency. The sampled signal is sent to the clutter filter (MTI filter) 37. The clutter filter 37 has a high-pass function, and removes the Doppler shift frequency component (low frequency component) of an internal organ whose motion is relatively slow from each Doppler signal. Then, the clutter filter 37 extracts a Doppler shift frequency component (high frequency component) of the blood current whose motion is relatively fast.

The auto-correlator 39 obtains the auto-correlation function of, e.g., 32 Doppler signals obtained for a period of 1/PRF every sample point. An output of the clutter filter 37 is expressed by Z (i, Δt) and its complex conjugate is expressed by Z*(i, Δt). In this case, Δ is 1/PRF and i is a data number. If the number of data items of the auto-correlation calculation is M, the auto-correlation function C(τ) can be obtained by the following equation:

$$C(\tau) = (1/M) \cdot \sum_{i=0}^{M-1} (Z(i, \Delta t) \cdot Z(i, \Delta t)$$

The calculator 41 calculates the average frequency $f_{average}$, variance $\sigma^2$, and power P every sample point based on the auto-correlation function C(τ) by the following equation.

$$f_{average} = (1/2\pi \cdot \Delta t) \cdot \tan^{-1}\{Im(C(\Delta t))/Re(C(\Delta t))\}$$
$$\sigma^2 = (2/(2\pi \cdot \Delta T)^2) \cdot \{1 - |C(\Delta t)|/C(0)\}$$
$$P = C(0)$$

wherein Re(C(Δt)) is a real part, and Im(C(Δt) is an imaginary part.

As is known, in the calculation of the auto-correlation, the number of data items (observing time) may be about 1/10 as compared with FFT. In other words, the average frequency of the large number of sample points can be calculated at a real time. Data of the average frequency is sent to the monitor 29 through a Doppler memory 43, and a digital scan converter 27 so as to be displayed as a color blood current image.

Figure 7:
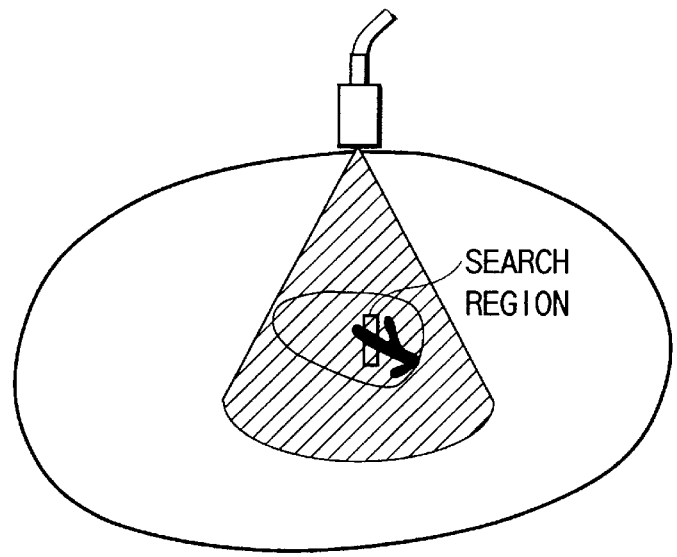
FIG. 7 is a view showing a scan region and a search region.

A time curve unit 45 is supplied with data such as the average frequency of the plurality of sample points in the search region from the Doppler memory 43. As shown in FIG. 7, the search region is set on the B mode image or the color blood current image to have an arbitrary size and depth.

Figure 8:
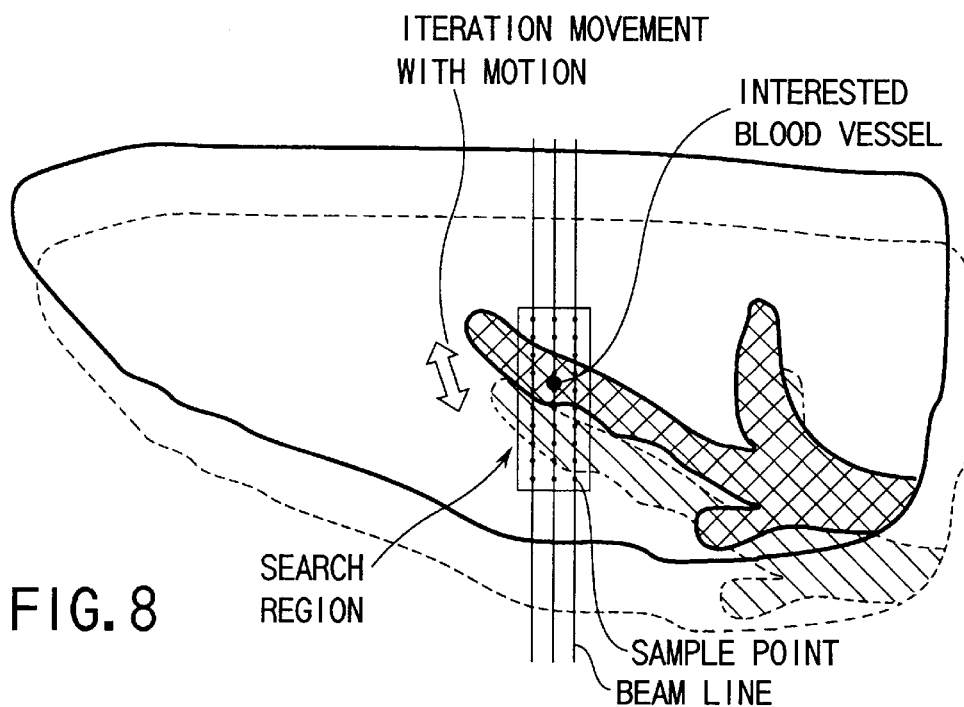
FIG. 8 is a specific view showing the search region.

As shown in FIG. 8, the blood vessel does not stay at a fixed location, but moves by the breath motion and the pulsation. Due to this motion, the average frequency of the interested blood vessel cannot be continuously observed at the same position (sample point). For this reason, according to the present invention, the concept of the search region is introduced. The search region is set to surround the moving range of the interested blood vessel. In other words, the size and the depth of the search region are set such that the sample point, which is positioned on the interested blood vessel, always exists in the search region.

Figure 6:
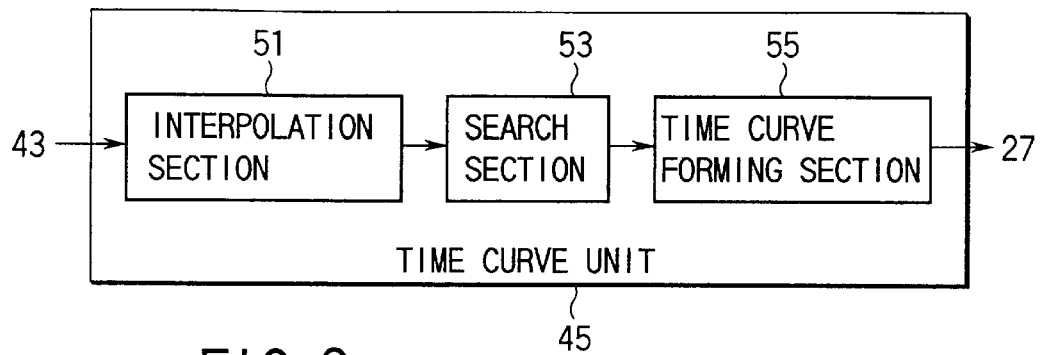
FIG. 6 is a block diagram of a time curve unit of FIG. 5.

As shown in FIG. 6, the time curve unit 45 comprises an interpolation section 51, a search section 53, and a time curve forming section 55. The interpolation section 51 spatially interpolates data of e.g., average frequency in the search region as required. The search section 53 picks up the sample point positioned on the interested blood vessel from the plurality of sample points in the search region in accordance with a predetermined rule to be described later.

Two kinds of rules are provided to pick up the sample point positioned on the interested blood vessel from the plurality of samples in the search region. Any one of the rules may be mounted. Or, both rules may be mounted to be selectively used by the operator.

(First rule)

Power of all sample points in the search region is compared to select the maximum power. Then, the sample point showing the selected maximum power is regarded as the sample point, which is positioned on the interested blood vessel, to be picked up.

(Second rule)

The average frequencies of all sample points in the search region are compared to select the maximum average frequency. Then, the sample point showing the selected maximum average frequency is regarded as the sample point, which is positioned on the interested blood vessel, to be picked up.

The time curve forming section 55 forms various time curves of the blood current of the interested blood vessel by the average frequency, variance, and power of the sample point picked up by either rule. The time curve is displayed as a graph on the monitor 29 through the digital scan converter 27.

Figure 9A:
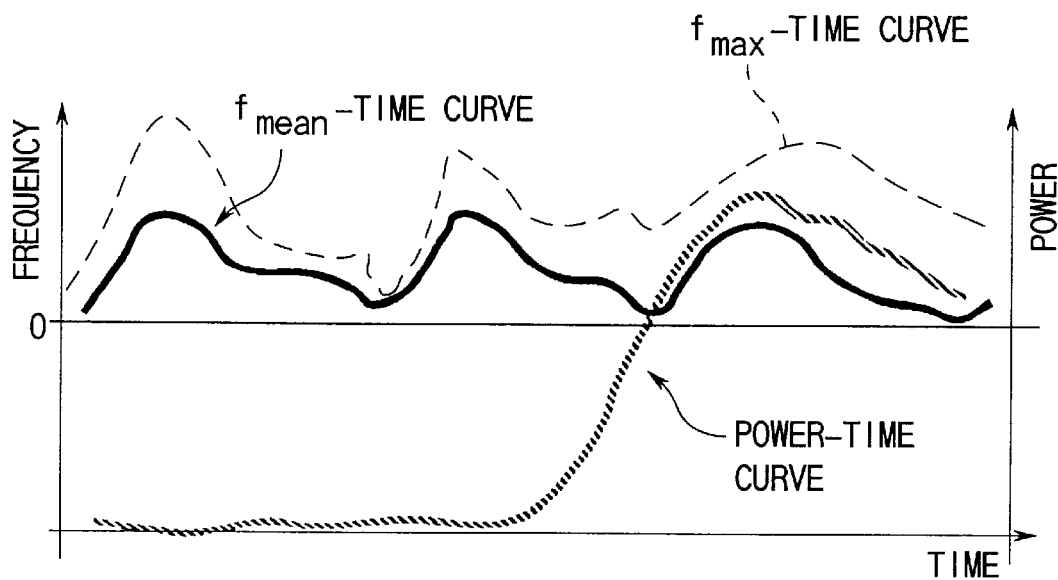
FIG. 9A is a view showing one example of the time curve.

As the time curves formed by the time curve forming section 55, as shown in FIG. 9A, there are the time curve of the average frequency (faverage) of the sample point picked up by the first or second rule, the time curve of the power (maximum power) of the sample point picked up by the first rule, and the time curve of the maximum frequency of the sample point picked up by the first or second rule. In this case, the maximum frequency $f_{max}$ can be estimated from the average frequency faverage and variance σ by $$f_{max} = f_{average} + K \cdot \sigma.$$

Figure 9B:
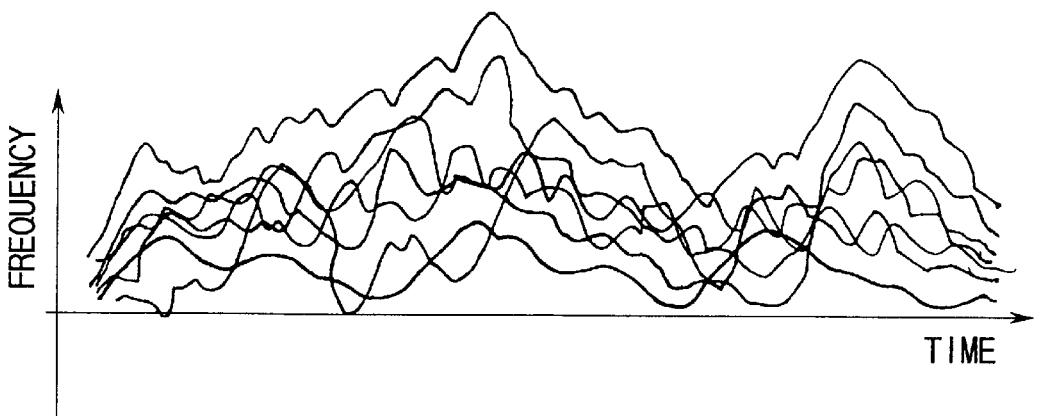
FIG. 9B is a view showing a display example of the time curve.
Figure 10A:
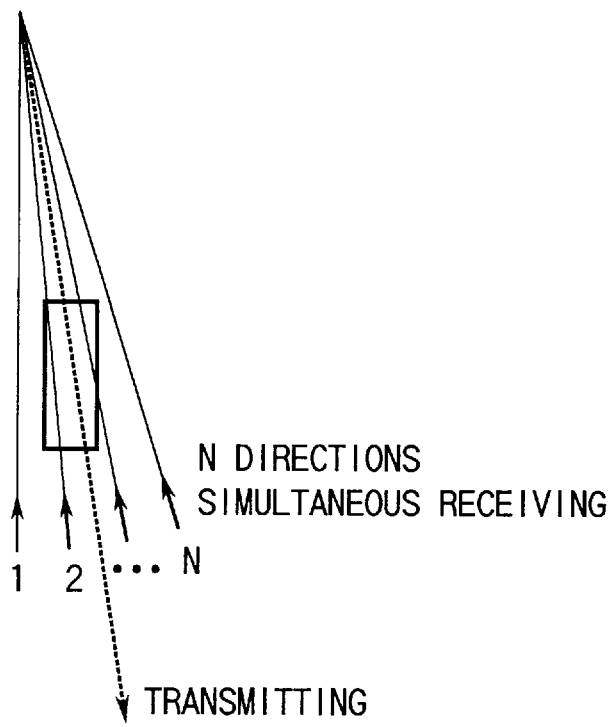
FIG. 10A is a view explaining a first receiving and transmitting method for achieving predetermined time resolution.
Figure 10B:
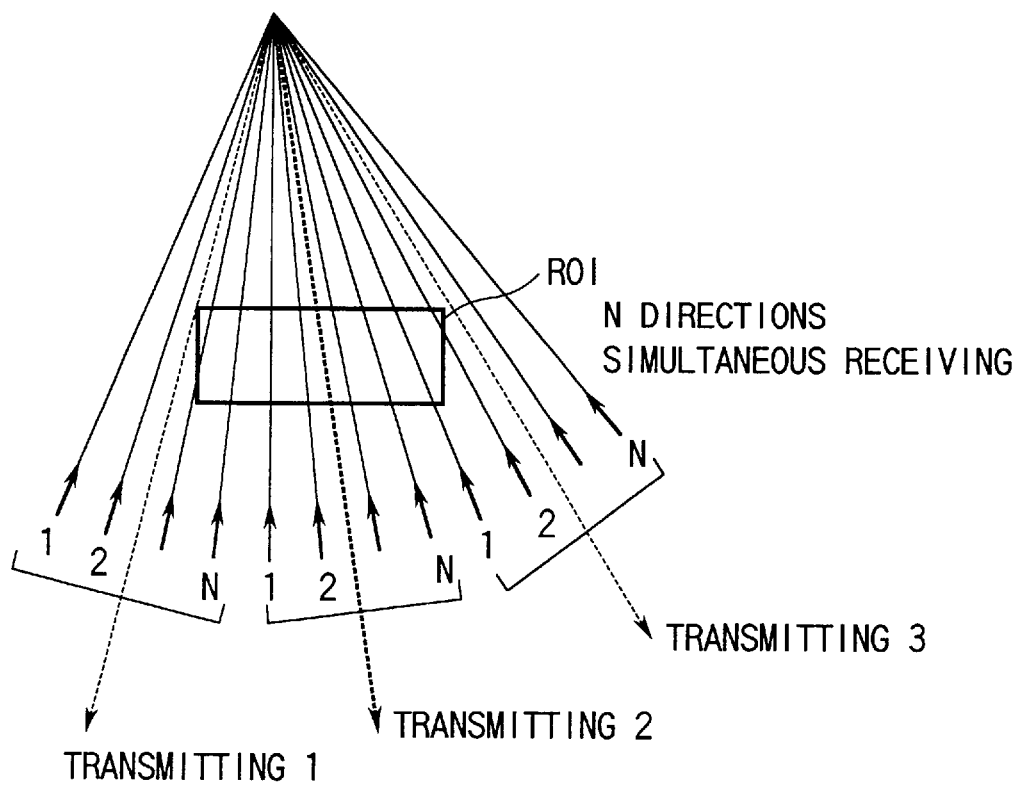
FIG. 10B is a view explaining a second receiving and transmitting method for achieving predetermined time resolution.

The time curve is not limited to the picked up sample point as shown in FIG. 9B. The time curves such as the average frequency of all sample points in the search region may be simultaneously displayed on the same screen.

The simultaneous display can provide an image, which approximates the Doppler image due to the spectrum Doppler. Also, the simultaneous display may provide new and useful data, which is different from the Doppler image.

Such a time curve may be described simply by a line. However, the time curve may be displayed by various display methods. For example, brightness may be modulated in accordance with power, or color may be modulated in accordance with variance.

After plural Doppler images were in a Doppler memory by 'Freeze' operation, an ROI is set on the memorized images and a spectrum Doppler image for blood vessels in the ROI is formed.

Figure 15:
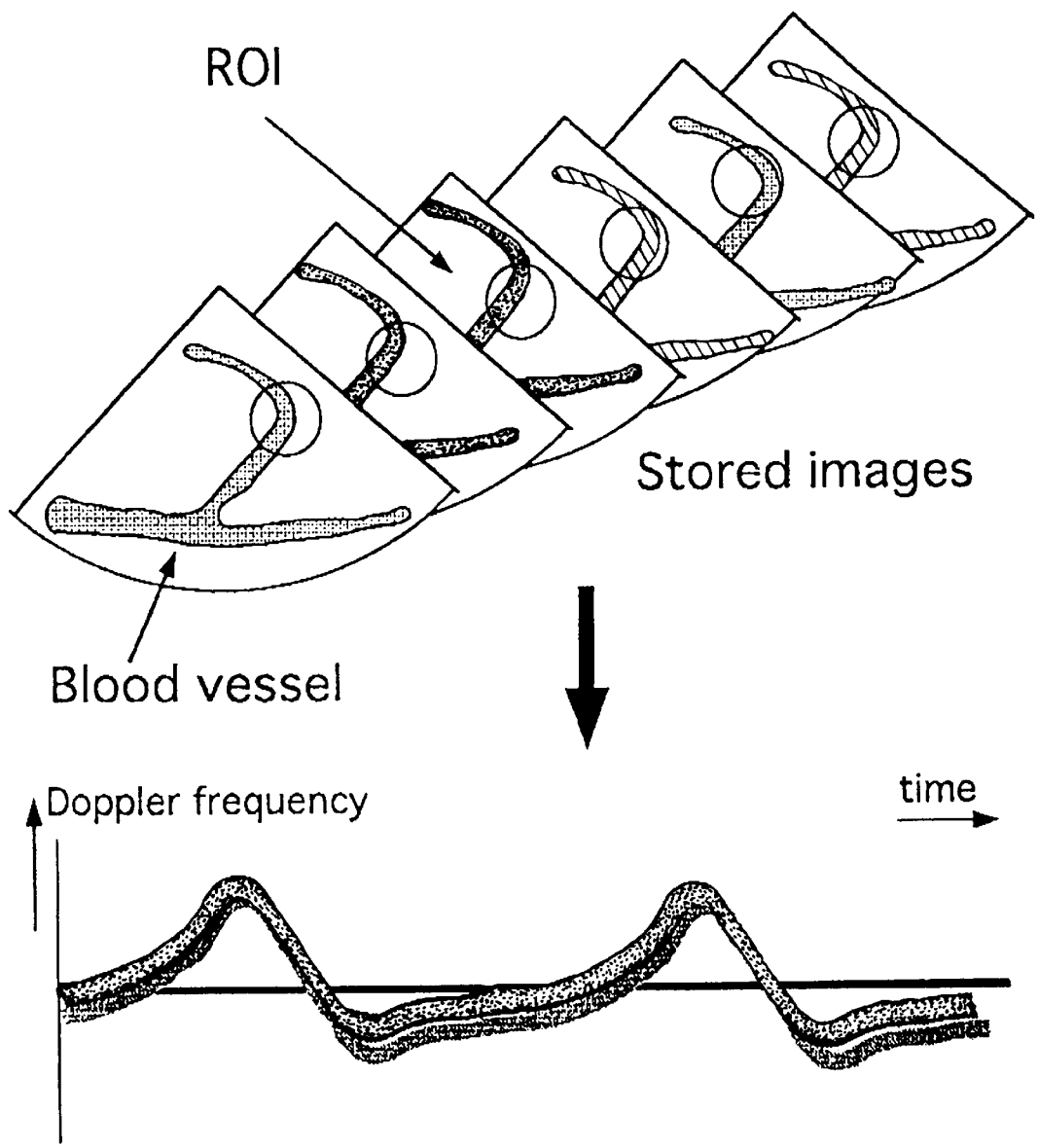
FIG. 15 is a view showing the ROI set on the moving blood vessel.

An ROI is set to cover a blood vessel moving to every each frame as shown in FIG. 15. The time curves of the average frequency for a plurality of pixels in the ROI are displayed simultaneously while modulating brightness in accordance with the power for each pixel. All kinds of indexes can be calculated from the spectrum Doppler image with a method as before.

According to the above-explained embodiment, the sample point positioned on the interested blood vessel moving by influence of the motion such as the breath motion and the pulsation is searched. As a result, the time curve of the average frequency can be obtained with high accuracy. Also, various indexes can be calculated with high accuracy from the time curve.

Moreover, according to the above-explained embodiment, since the average frequency is used, unfavorable influence of contrast agent can be reduced. The average frequency can be calculated by use of the known CFM unit. As a result, there is no need of the conventional process for obtaining the average frequency from the frequency spectrum by the gravity calculation. In consideration of the process for obtaining the average frequency $f_{average}$, only the auto-correlation function C (Δt) may be obtained. As a result, there may be set the number of calculations in which the number of multiplications is M and the number of additions is M-1 when the number of data items is M. On the other hand, in FFT, the number of calculations of (M·r)/2 is needed. In this case, M=$2^r$. Moreover, in FFT, the following process is further needed to obtain the average frequency.

$$f_{average} = \left(\sum_{i=1}^{M} f_i \cdot S_i\right) / \left(\sum_{i=1}^{M} S_i\right)$$

In this case, $S_i$ is a power spectrum of a frequency component $f_i$.

The number of the auto-correlation calculation processes is smaller than the number of FFT calculation processes as shown by M/(M·r)/2)=¼
wherein r=8, and M=258.

Generally, the number of data items of the auto-correlation is 32. In consideration of the number of data items, the number of the auto-correlation calculation processes is considerably smaller than the number of FFT calculation processes as shown by the following equation:

$$M'/(M \cdot r)/2) = 1/32$$

In consideration of the process for calculating the average frequency from the spectrum of FFT, the number of the auto-correlation calculation processes may be about 1/40 of the FFT.

Thus, as compared with the case in which the average frequency is obtained by FFT, the number of processes can be drastically reduced by directly obtaining the average frequency by the auto-correlation.

In the conventional spectrum Doppler, the echo may be received from one direction passing through the sample volume. In the present invention, the echo must be received from a plurality of directions covering the search regions. Due to this, the reduction of time resolution may be brought about. Specifically, necessary time resolution is, for example, 100 Hz. In other words, the average frequency of each sample point in the search region must be calculated every 1/100 seconds.

According to the present invention, time resolution of 100 Hz can be realized by a parallel simultaneous receiving technique and the limitation of the scan range to the search region. In this case, as the main parameters of time resolution (frame rate), there are pulse repetition frequency PRF, the number of data items (observing time) of auto-correlation process, the number of beam directions R covering the search region, and number of simultaneous receiving directions N (the echo is received from N direction simultaneously with one transmission).

Among these parameters, R is determined, depending on the size of the search region. N, which is necessary to achieve the frame rate of 100 Hz, can be obtained by the following equation:

$$100\ Hz = PRF/(M \times (R \cdot N))$$

Figure 11:
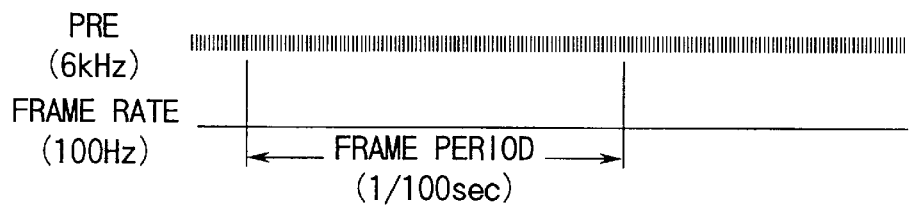
FIG. 11 is a view showing predetermined time resolution.
Figure 12:
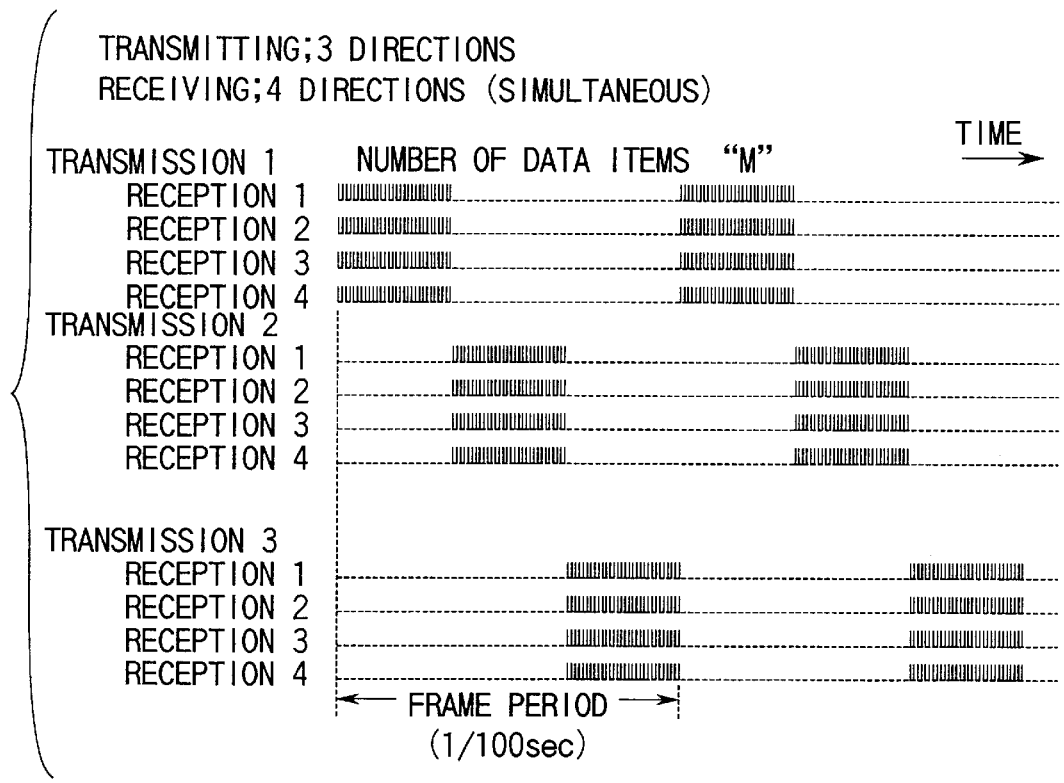
FIG. 12 is a time chart of the receiving and transmitting method of FIG. 10B.

For example, as shown in FIG. 11, it is assumed that PRF=6 kHz, the number of data times M=15, and R=16. N, which is necessary to achieve the frame rate of 100 Hz, is set to 4. FIG. 12 shows a time chart of four direction parallel simultaneous receivings. The number of beam directions R=12.

Thus, the number of directions N of the simultaneous receivings is calculated by a CPU 47 in accordance with the size of the search region. As a result, time resolution of 100 Hz can be achieved.

Figure 13:
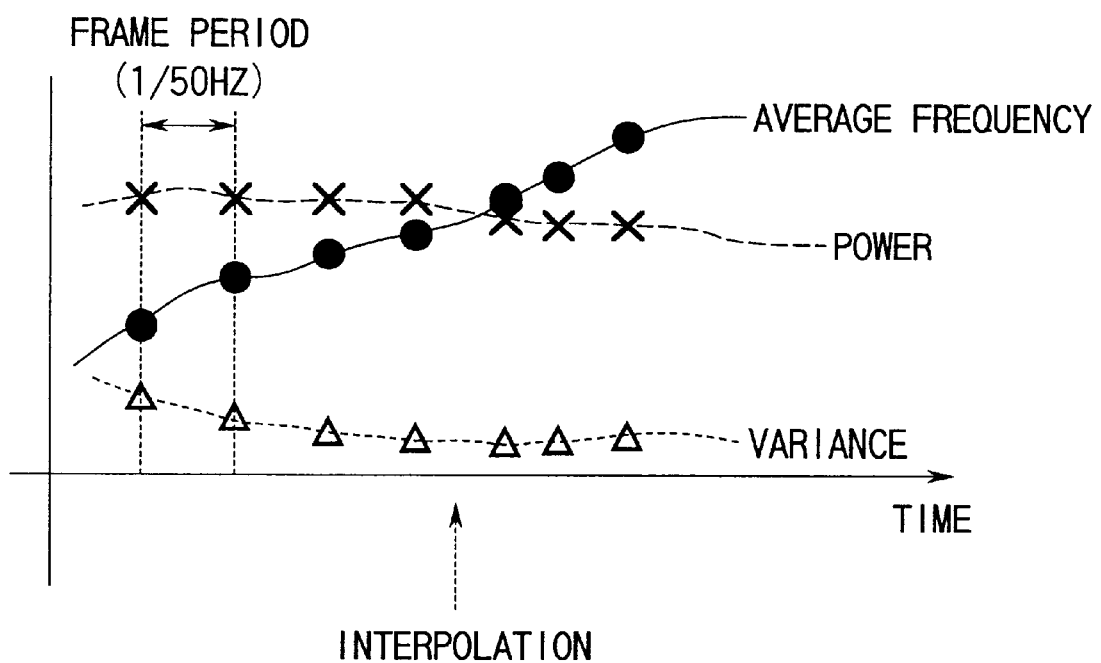
FIG. 13 is a view showing a time curve of e.g., average frequency interpolated by an interpolation section 51 of FIG. 6.

There is, of course, a limitation in the number of directions N of the simultaneous receivings. Accordingly as the search region is enlarged, there may be a case in which the frame rate of 100 Hz cannot be achieved only by the increase in N. In such a case, the pulse repetition frequency PRF is increased in accordance with the depth of the search region (depth of a visual field). Also, the beam pitch may be enlarged so that the number of directions R is reduced. A small number of data items M is effective for high frame rate. Moreover, as shown in FIG. 13, the frame rate of 100 Hz may be seemingly achieved by interpolation.

Figure 14:
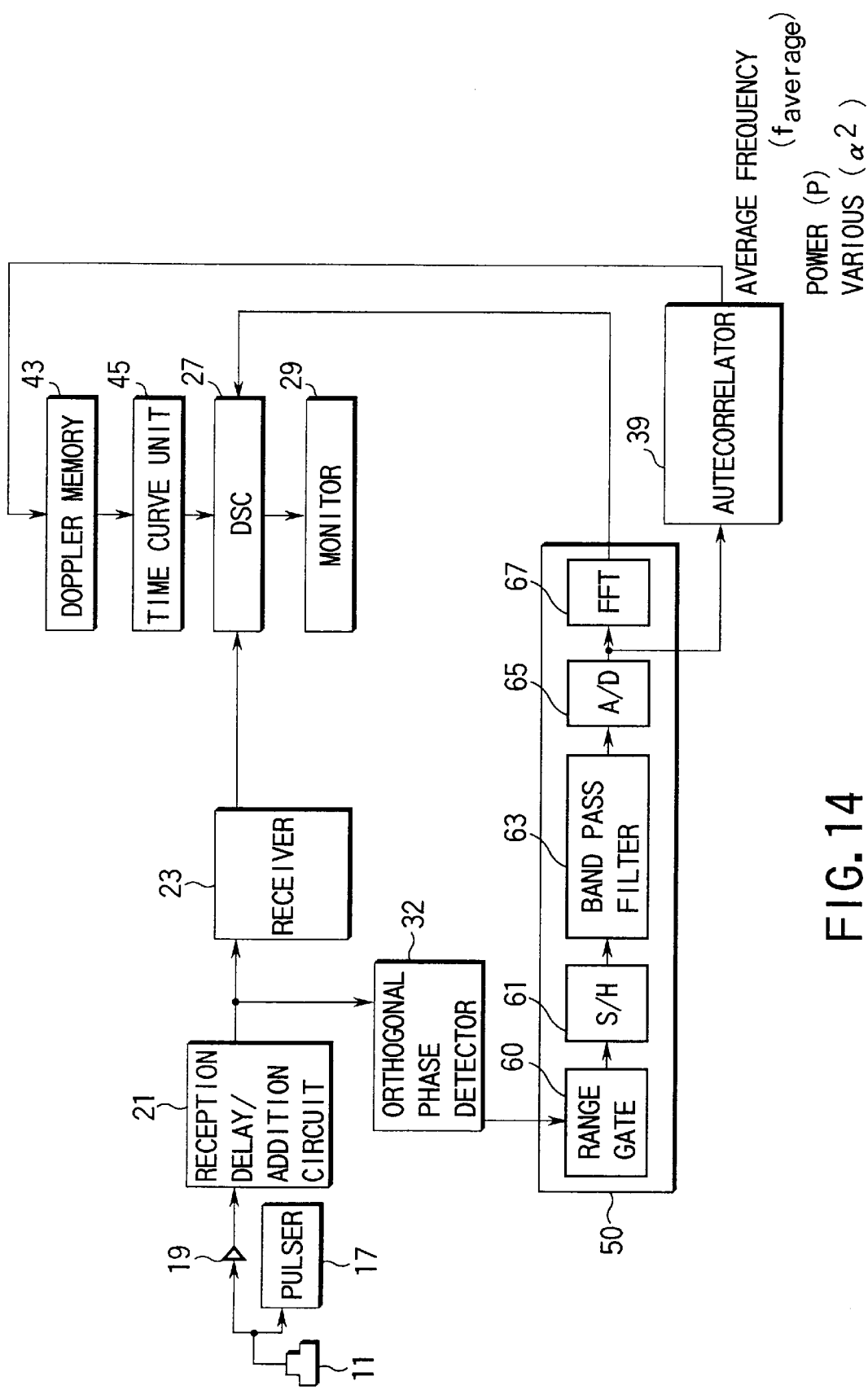
FIG. 14 is a view showing a modification of the ultrasonic diagnostic apparatus.

According to the present invention, as shown in FIG. 14, there can be also used a spectrum Doppler circuit 50, which comprises a range gate circuit 60, a sample hold circuit 61, a band pass filter 63, an analog digital converter 65, and a fast Fourier transformer (FFT) 67. In this case, the auto-correlator 39 is connected to the analog digital converter 65 to input the shift frequency signal of the blood current.

Additional advantages and modifications will readily occur to those skilled in the art. Therefore, the invention in its broader aspects is not limited to the specific details and representative devices shown and described herein. Accordingly, various modifications may be made without departing from the spirit or scope of the general inventive concept as defined by the appended claims and their equivalents.

I claim:

1. An ultrasonic diagnostic apparatus comprising:
    scanning means for scanning an interested region including an interested blood vessel of a subject so as to receive echo signals;
    means for detecting Doppler signals from the echo signals for sample points in the interested region;
    means for calculating an average frequency, a variance, and power at each of the sample points based on the Doppler signals;
    means for picking up out of the sample points phase, one sample point whose one of the average frequency, the variance, and power is characteristic of the sample points; and
    means for forming a time curve of the blood current based on at least one of the average frequency, the variance and power of the picked up sample point.

2. The apparatus according to claim 1, wherein said pick up means picks up the sample point showing maximum power as a sample point positioned on the interested blood vessel.

3. The apparatus according to claim 1, wherein said pick up means picks up the sample point showing a maximum average frequency as a sample point positioned on the interested blood vessel.

4. The apparatus according to claim 1, wherein said scanning means has means for forming the echo signals whose receiving directions are different from each other at one transmission time.

5. The apparatus according to claim 4, further comprising means for adjusting at least one of a pulse repetition frequency, a number of ultrasonic beam lines of said interested region, a number of receiving directions at one transmission and a number of data items of a frequency analysis so as to obtain said average frequency, the variance, and power on a predetermined time resolution.

6. The apparatus according to claim 1, further comprising means for time interpolating said time curve.

7. The apparatus according to claim 1, wherein the time curve is the time curve of the average frequency.

8. The apparatus according to claim 1, wherein the time curve is the time curve of the power.

9. The apparatus according to claim 1, further comprising means for estimating a maximum frequency based on the average frequency and the variance.

10. The apparatus according to claim 9, wherein said time curve is the time curve of the maximum frequency.

11. An ultrasonic diagnostic apparatus comprising:
    means for scanning a region of interest including an interested blood vessel of a subject by ultrasonic waves, and wherein echo signals whose receiving directions are different from each other are simultaneously generated with the scanning;
    means for adjusting the number of the echo signals simultaneously generated in accordance with a size of the region of interest;
    means for detecting Doppler signals of a blood current of the interested blood vessel from the echo signals;
    means for calculating an auto-correlation function of the Doppler signals;
    means for calculating an average frequency, a variance, and power based on the calculated auto-correlation function; and
    means for forming a time curve of the blood current based on at least one of the average frequency, the variance and power.

12. The apparatus according to claim 11, wherein the time curve is the time curve of the average frequency.

13. The apparatus according to claim 11, wherein the time curve is the time curve of the power.

14. The apparatus according to claim 11, further comprising means for estimating a maximum frequency based on the average frequency and the variance.

15. The apparatus according to claim 14, wherein the time curve is the time curve of the maximum frequency.

16. An ultrasonic diagnostic apparatus comprising:
    means for scanning an interested region including an interested blood vessel of a subject so as to receive echo signals;
    means for detecting Doppler signals from the echo signals for a plurality of sample points in the interested region;
    means for calculating an average frequency, a variance, and power based on the Doppler signals;
    means for forming time curves of the blood current based on at least one of the average frequency, the variance and power; and
    means for simultaneously displaying the time curves for a plurality of sample points.

17. The apparatus according to claim 16, wherein said display means modulates brightness in accordance with the power for each sample point.

18. The apparatus according to claim 16, wherein the time curve is the time curve of the average frequency.

19. The apparatus according to claim 16, wherein the time curve is the time curve of the power.

20. The apparatus according to claim 16, further comprising means for estimating a maximum frequency of each sample point based on the average frequency and the variance.

21. The apparatus according to claim 20, wherein the time curve is the time curve of the maximum frequency of each sample point.

22. A color Doppler apparatus comprising:

means for detecting a Doppler signal of each sample point in a set scanning region;

means for calculating an average frequency, a variance, and power based on the Doppler signal at each sample point;

means for storing data of the average frequency, the variance and power of each sample point over scanning of a plurality of frames;

means for obtaining color Doppler images corresponding to the stored frames based on data on said memory;

means for setting a region of interest having a predetermined size and a shape at a predetermined position on the obtained color Doppler image;

means for forming a plurality of time change curves of the sample points based on at least one of the stored average frequency, the variance, and power; and means for displaying the time curves on a same screen.

23. The apparatus according to claim 22, wherein said display means modulates brightness in accordance with the power for each sample point.

24. The apparatus according to claim 22, wherein the time curve is the time curve of the average frequency.

25. The apparatus according to claim 22, wherein the time curve is the time curve of the power.

26. The apparatus according to claim 22, further comprising means for estimating a maximum frequency of each sample point based on the average frequency and the variance.

27. The apparatus according to claim 26, wherein the time curve is the time curve of the maximum frequency of each sample point.

* * * * *